(12) United States Patent
Palese et al.

(10) Patent No.: US 9,936,940 B2
(45) Date of Patent: Apr. 10, 2018

(54) METHOD AND APPARATUS FOR COUPLING SOFT TISSUE TO BONE

(71) Applicant: Biomet Sports Medicine, LLC, Warsaw, IN (US)

(72) Inventors: Christopher M. Palese, Warsaw, IN (US); Gregory J. Denham, Warsaw, IN (US); Dan Norton, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 403 days.

(21) Appl. No.: 14/019,646

(22) Filed: Sep. 6, 2013

(65) Prior Publication Data

US 2014/0364906 A1 Dec. 11, 2014

Related U.S. Application Data

(60) Provisional application No. 61/832,344, filed on Jun. 7, 2013.

(51) Int. Cl.
*A61B 17/04* (2006.01)
*A61B 17/00* (2006.01)
*A61B 17/06* (2006.01)

(52) U.S. Cl.
CPC .......... *A61B 17/0401* (2013.01); *A61B 2017/00884* (2013.01); *A61B 2017/0403* (2013.01);
(Continued)

(58) Field of Classification Search
CPC ........ A61B 17/0401; A61B 2017/0409; A61B 2017/0414; A61B 2017/0438; A61B 2017/044; A61B 2017/0445; A61B 2017/0446; A61B 2017/0451–2017/0454; A61B 2017/0458–2017/0464;
(Continued)

(56) References Cited

U.S. PATENT DOCUMENTS

| 3,623,192 A | 11/1971 | Papazian |
| 4,210,148 A | 7/1980 | Stivala |

(Continued)

FOREIGN PATENT DOCUMENTS

| SU | 1600713 A | 10/1990 |
| WO | 9203980 A | 3/1992 |

(Continued)

*Primary Examiner* — Victor Nguyen
*Assistant Examiner* — Jonathan Hollm
(74) *Attorney, Agent, or Firm* — Schwegman Lundberg & Woessner, P.A.

(57) ABSTRACT

A method for securing a suture to bone can include loading the suture in a distal opening of an inserter of an assembly. The suture can be coupled to soft tissue. The assembly can include the inserter, an anchor carried by the inserter, a distal tip and a driver each coupled to the inserter. A hole can be formed in the bone with the distal tip, and the distal opening and a portion of the suture can be positioned in the hole. The driver can be actuated to allow movement relative to the inserter and can be advanced in a first direction to drive the anchor about the inserter into the hole to secure the distal tip, anchor and suture to the bone with an absence of a knot. The driver can be moved in a second direction to remove the inserter from the distal tip, anchor and suture.

27 Claims, 9 Drawing Sheets

(52) U.S. Cl.
CPC ... *A61B 2017/044* (2013.01); *A61B 2017/045* (2013.01); *A61B 2017/0409* (2013.01); *A61B 2017/0412* (2013.01); *A61B 2017/0414* (2013.01); *A61B 2017/0445* (2013.01); *A61B 2017/0453* (2013.01); *A61B 2017/06042* (2013.01); *A61B 2017/06185* (2013.01)

(58) Field of Classification Search
CPC ... A61F 2/0811; A61F 2002/0817–2002/0829; A61F 2002/0841–2002/0858; A61F 2002/0876; A61F 2002/0888
USPC ............... 606/232, 311–312; 623/13.14
See application file for complete search history.

(56) References Cited

U.S. PATENT DOCUMENTS

| | | |
|---|---|---|
| 4,532,926 A | 8/1985 | O'Holla |
| 4,632,100 A | 12/1986 | Somers et al. |
| 4,741,330 A | 5/1988 | Hayhurst |
| 4,796,612 A | 1/1989 | Reese |
| 4,898,156 A | 2/1990 | Gatturna et al. |
| 4,899,743 A | 2/1990 | Nicholson et al. |
| 4,927,421 A | 5/1990 | Goble et al. |
| 4,950,270 A | 8/1990 | Bowman et al. |
| 4,968,315 A | 11/1990 | Gatturna |
| 5,013,316 A | 5/1991 | Goble et al. |
| 5,037,422 A | 8/1991 | Hayhurst et al. |
| 5,139,499 A | 8/1992 | Small et al. |
| 5,139,520 A | 8/1992 | Rosenberg |
| 5,141,520 A | 8/1992 | Goble et al. |
| 5,152,790 A | 10/1992 | Rosenberg et al. |
| 5,156,616 A | 10/1992 | Meadows et al. |
| 5,192,303 A | 3/1993 | Gatturna et al. |
| 5,207,679 A * | 5/1993 | Li .................. A61B 17/0401 606/139 |
| 5,219,359 A | 6/1993 | McQuilkin et al. |
| 5,224,946 A | 7/1993 | Hayhurst et al. |
| 5,234,430 A | 8/1993 | Huebner |
| 5,258,016 A | 11/1993 | Dipoto et al. |
| 5,269,784 A | 12/1993 | Mast |
| 5,336,240 A | 8/1994 | Metzler et al. |
| 5,354,298 A | 10/1994 | Lee et al. |
| 5,354,299 A | 10/1994 | Coleman |
| 5,372,604 A | 12/1994 | Trott |
| 5,374,269 A | 12/1994 | Rosenberg |
| 5,383,905 A | 1/1995 | Golds et al. |
| 5,417,712 A | 5/1995 | Whittaker et al. |
| 5,423,858 A | 6/1995 | Bolanos et al. |
| 5,423,860 A | 6/1995 | Lizardi et al. |
| 5,443,509 A | 8/1995 | Boucher et al. |
| 5,456,685 A | 10/1995 | Huebner |
| 5,466,243 A | 11/1995 | Schmieding et al. |
| 5,472,452 A | 12/1995 | Trott |
| 5,478,353 A | 12/1995 | Yoon |
| 5,500,001 A | 3/1996 | Trott |
| 5,522,844 A | 6/1996 | Johnson |
| 5,527,341 A | 6/1996 | Gogolewski et al. |
| 5,527,342 A | 6/1996 | Pietrzak et al. |
| 5,527,343 A | 6/1996 | Bonutti |
| 5,543,012 A | 8/1996 | Watson et al. |
| 5,545,180 A | 8/1996 | Le et al. |
| 5,569,306 A | 10/1996 | Thal |
| 5,575,801 A | 11/1996 | Habermeyer et al. |
| 5,578,057 A | 11/1996 | Wenstrom, Jr. |
| 5,584,835 A | 12/1996 | Greenfield |
| 5,591,207 A | 1/1997 | Coleman |
| 5,601,558 A | 2/1997 | Torrie et al. |
| 5,632,748 A | 5/1997 | Beck, Jr. et al. |
| 5,634,926 A | 6/1997 | Jobe |
| 5,643,320 A | 7/1997 | Lower et al. |
| 5,658,313 A | 8/1997 | Thal |
| 5,665,112 A | 9/1997 | Thal |
| 5,671,695 A | 9/1997 | Schroeder |
| 5,681,333 A | 10/1997 | Burkhart et al. |
| 5,683,401 A | 11/1997 | Schmieding et al. |
| 5,683,419 A | 11/1997 | Thal |
| 5,688,285 A | 11/1997 | Yamada |
| 5,690,676 A | 11/1997 | DiPoto et al. |
| 5,697,950 A | 12/1997 | Fucci et al. |
| 5,702,397 A | 12/1997 | Goble et al. |
| 5,702,398 A | 12/1997 | Tarabishy |
| 5,709,708 A | 1/1998 | Thal |
| 5,718,706 A | 2/1998 | Roger |
| 5,720,765 A | 2/1998 | Thal |
| 5,725,541 A | 3/1998 | Anspach, III et al. |
| 5,725,557 A | 3/1998 | Gatturna et al. |
| 5,741,282 A | 4/1998 | Anspach, III et al. |
| 5,769,894 A | 6/1998 | Ferragamo |
| 5,782,864 A | 7/1998 | Lizardi |
| 5,800,436 A | 9/1998 | Lerch |
| 5,814,072 A | 9/1998 | Bonutti |
| 5,891,146 A | 4/1999 | Simon et al. |
| 5,891,168 A | 4/1999 | Thal |
| RE36,289 E | 8/1999 | Le et al. |
| 5,935,134 A | 8/1999 | Pedlick et al. |
| 5,948,001 A | 9/1999 | Larsen |
| 5,948,002 A | 9/1999 | Bonutti |
| 5,951,560 A | 9/1999 | Simon et al. |
| 5,951,590 A | 9/1999 | Goldfarb |
| 5,964,769 A | 10/1999 | Wagner et al. |
| 5,980,558 A | 11/1999 | Wiley |
| 5,993,459 A | 11/1999 | Larsen et al. |
| 6,010,525 A | 1/2000 | Bonutti et al. |
| 6,013,077 A | 1/2000 | Harwin |
| 6,013,083 A | 1/2000 | Bennett |
| 6,027,523 A | 2/2000 | Schmieding |
| 6,041,485 A | 3/2000 | Pedlick et al. |
| 6,045,573 A | 4/2000 | Wenstrom, Jr. et al. |
| 6,056,751 A | 5/2000 | Fenton, Jr. |
| 6,063,106 A | 5/2000 | Gibson |
| 6,093,201 A | 7/2000 | Cooper et al. |
| 6,093,301 A | 7/2000 | Van Atta |
| 6,099,547 A | 8/2000 | Gellman et al. |
| 6,110,207 A | 8/2000 | Eichhorn et al. |
| 6,117,160 A | 9/2000 | Bonutti |
| 6,117,161 A | 9/2000 | Li et al. |
| 6,123,711 A | 9/2000 | Winters |
| 6,126,677 A | 10/2000 | Ganaja et al. |
| 6,149,669 A | 11/2000 | Li |
| 6,200,330 B1 | 3/2001 | Benderev et al. |
| 6,241,749 B1 | 6/2001 | Rayhanabad |
| 6,245,082 B1 | 6/2001 | Gellman et al. |
| 6,280,474 B1 | 8/2001 | Cassidy et al. |
| 6,293,961 B2 | 9/2001 | Schwartz et al. |
| 6,296,659 B1 | 10/2001 | Foerster |
| 6,306,159 B1 | 10/2001 | Schwartz et al. |
| 6,319,271 B1 | 11/2001 | Schwartz et al. |
| 6,328,758 B1 | 12/2001 | Tornier et al. |
| 6,391,030 B1 | 5/2002 | Wagner et al. |
| 6,423,065 B2 | 7/2002 | Ferree |
| 6,432,123 B2 | 8/2002 | Schwartz et al. |
| 6,464,713 B2 | 10/2002 | Bonutti |
| 6,491,714 B1 | 12/2002 | Bennett |
| 6,514,274 B1 | 2/2003 | Boucher et al. |
| 6,518,200 B2 | 2/2003 | Lin |
| 6,520,980 B1 | 2/2003 | Foerster |
| 6,524,317 B1 | 2/2003 | Ritchart et al. |
| 6,527,794 B1 | 3/2003 | McDevitt et al. |
| 6,533,795 B1 | 3/2003 | Tran et al. |
| 6,540,770 B1 | 4/2003 | Tornier et al. |
| 6,544,281 B2 | 4/2003 | Elattrache et al. |
| 6,547,800 B2 | 4/2003 | Foerster et al. |
| 6,551,330 B1 | 4/2003 | Bain et al. |
| 6,554,852 B1 | 4/2003 | Oberlander |
| 6,569,187 B1 | 5/2003 | Bonutti et al. |
| 6,575,987 B2 | 6/2003 | Gellman et al. |
| 6,582,453 B1 | 6/2003 | Tran et al. |
| 6,585,730 B1 | 7/2003 | Foerster |
| 6,605,096 B1 | 8/2003 | Ritchart |
| 6,635,073 B2 | 10/2003 | Bonutti |
| 6,638,279 B2 | 10/2003 | Bonutti |
| 6,652,561 B1 | 11/2003 | Tran |
| 6,660,008 B1 | 12/2003 | Foerster et al. |

(56) References Cited

U.S. PATENT DOCUMENTS

| | | |
|---|---|---|
| 6,660,023 B2 | 12/2003 | McDevitt et al. |
| 6,673,094 B1 * | 1/2004 | McDevitt ............ A61B 17/0401 606/104 |
| 6,712,830 B2 | 3/2004 | Esplin |
| 6,770,076 B2 | 8/2004 | Foerster |
| 6,780,198 B1 | 8/2004 | Gregoire et al. |
| 6,855,157 B2 | 2/2005 | Foerster et al. |
| 6,984,241 B2 | 1/2006 | Lubbers et al. |
| 6,986,781 B2 | 1/2006 | Smith |
| 7,041,120 B2 | 5/2006 | Li et al. |
| 7,056,333 B2 | 6/2006 | Walshe |
| 7,081,126 B2 | 7/2006 | McDevitt et al. |
| 7,083,638 B2 | 8/2006 | Foerster |
| 7,090,690 B2 | 8/2006 | Foerster et al. |
| 7,144,415 B2 | 12/2006 | Del Rio et al. |
| 7,153,312 B1 | 12/2006 | Torrie et al. |
| 7,156,864 B2 | 1/2007 | Lintner |
| 7,232,455 B2 | 6/2007 | Pedlick et al. |
| 7,235,100 B2 | 6/2007 | Martinek |
| 7,329,272 B2 * | 2/2008 | Burkhart ............ A61B 17/0401 606/148 |
| 7,517,357 B2 | 4/2009 | Abrams et al. |
| 7,572,283 B1 | 8/2009 | Meridew |
| 7,585,311 B2 | 9/2009 | Green et al. |
| 7,993,369 B2 | 8/2011 | Dreyfuss |
| 8,057,524 B2 | 11/2011 | Meridew |
| 8,075,588 B2 | 12/2011 | Berberich et al. |
| 8,133,258 B2 | 3/2012 | Foerster et al. |
| 8,317,829 B2 | 11/2012 | Foerster et al. |
| 8,430,909 B2 | 4/2013 | Dreyfuss |
| 2001/0008971 A1 | 7/2001 | Schwartz et al. |
| 2001/0018597 A1 | 8/2001 | Gellman et al. |
| 2001/0051815 A1 | 12/2001 | Esplin |
| 2001/0051816 A1 | 12/2001 | Enzerink et al. |
| 2002/0019649 A1 | 2/2002 | Sikora et al. |
| 2002/0029066 A1 | 3/2002 | Foerster |
| 2002/0077631 A1 | 6/2002 | Lubbers et al. |
| 2002/0111653 A1 | 8/2002 | Foerster |
| 2002/0128684 A1 | 9/2002 | Foerster |
| 2002/0169478 A1 | 11/2002 | Schwartz et al. |
| 2002/0188305 A1 | 12/2002 | Foerster et al. |
| 2003/0018358 A1 | 1/2003 | Saadat |
| 2003/0088270 A1 | 5/2003 | Lubbers et al. |
| 2003/0105591 A1 | 6/2003 | Hagiwara |
| 2003/0149448 A1 | 8/2003 | Foerster et al. |
| 2003/0167072 A1 | 9/2003 | Oberlander |
| 2003/0181925 A1 | 9/2003 | Bain et al. |
| 2003/0191498 A1 | 10/2003 | Foerster et al. |
| 2003/0195528 A1 | 10/2003 | Ritchart |
| 2003/0195563 A1 | 10/2003 | Foerster |
| 2003/0195564 A1 | 10/2003 | Tran et al. |
| 2003/0204204 A1 | 10/2003 | Bonutti |
| 2003/0236555 A1 | 12/2003 | Thornes |
| 2004/0002735 A1 | 1/2004 | Lizardi et al. |
| 2004/0024420 A1 | 2/2004 | Lubbers et al. |
| 2004/0044366 A1 | 3/2004 | Bonutti et al. |
| 2004/0102779 A1 | 5/2004 | Nesper et al. |
| 2004/0116961 A1 | 6/2004 | Nesper et al. |
| 2004/0133238 A1 | 7/2004 | Cerier |
| 2004/0138706 A1 * | 7/2004 | Abrams ............ A61B 17/0401 606/232 |
| 2004/0193217 A1 | 9/2004 | Lubbers et al. |
| 2004/0225325 A1 | 11/2004 | Bonutti |
| 2004/0243178 A1 | 12/2004 | Haut et al. |
| 2004/0254609 A1 | 12/2004 | Esplin |
| 2004/0267317 A1 | 12/2004 | Higgins et al. |
| 2005/0027307 A1 | 2/2005 | Schwartz et al. |
| 2005/0055052 A1 | 3/2005 | Lombardo et al. |
| 2005/0240199 A1 | 10/2005 | Martinek et al. |
| 2005/0240226 A1 | 10/2005 | Foerster et al. |
| 2005/0245932 A1 | 11/2005 | Fanton et al. |
| 2005/0283158 A1 | 12/2005 | West |
| 2005/0288682 A1 | 12/2005 | Howe |
| 2006/0106423 A1 | 5/2006 | Weisel et al. |
| 2006/0116719 A1 | 6/2006 | Martinek |
| 2006/0178702 A1 | 8/2006 | Pierce et al. |
| 2006/0235413 A1 | 10/2006 | Denham et al. |
| 2006/0271060 A1 | 11/2006 | Gordon |
| 2006/0271105 A1 | 11/2006 | Foerster et al. |
| 2006/0293710 A1 | 12/2006 | Foerster et al. |
| 2007/0142861 A1 | 6/2007 | Burkhart |
| 2007/0270907 A1 * | 11/2007 | Stokes ............... A61B 17/0469 606/232 |
| 2008/0082128 A1 * | 4/2008 | Stone ................ A61B 17/0401 606/232 |
| 2008/0208253 A1 * | 8/2008 | Dreyfuss ............ A61B 17/0401 606/232 |
| 2009/0312794 A1 | 12/2009 | Nason et al. |
| 2010/0004683 A1 | 1/2010 | Hoof et al. |
| 2010/0262184 A1 | 10/2010 | Dreyfuss |
| 2013/0103083 A1 | 4/2013 | Baird |
| 2013/0144334 A1 | 6/2013 | Bouduban et al. |

FOREIGN PATENT DOCUMENTS

| | | |
|---|---|---|
| WO | 0154586 A | 8/2001 |
| WO | 0167962 A | 9/2001 |
| WO | 0211630 A | 2/2002 |
| WO | 0221998 A | 3/2002 |
| WO | 03065904 A | 8/2003 |
| WO | 2004062506 A | 7/2004 |
| WO | 2005112786 A | 12/2005 |
| WO | 2005112788 A | 12/2005 |
| WO | 2006060035 A | 6/2006 |
| WO | 2006067548 A | 6/2006 |
| WO | 2006128092 A | 11/2006 |
| WO | 2007084714 A | 7/2007 |

* cited by examiner

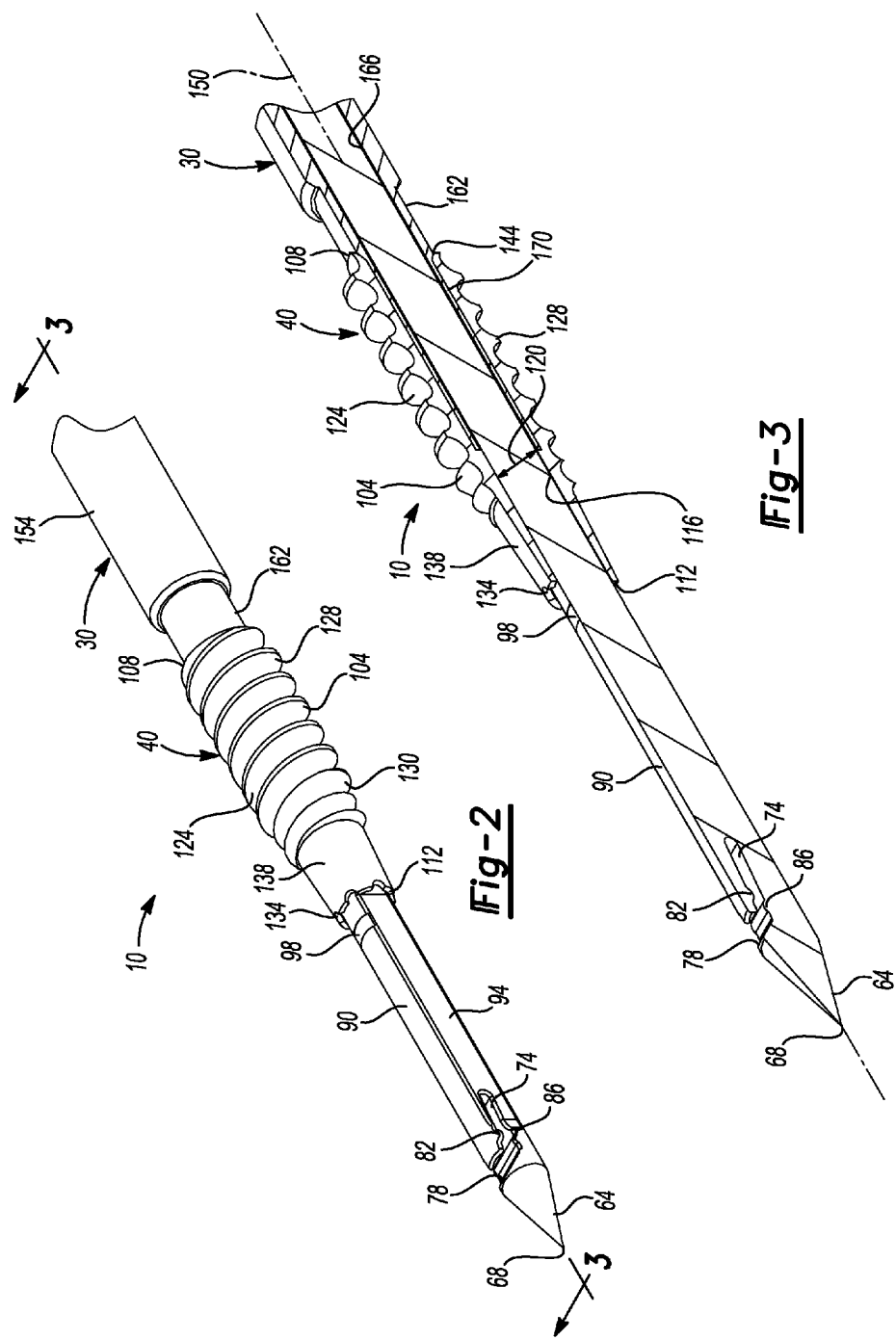

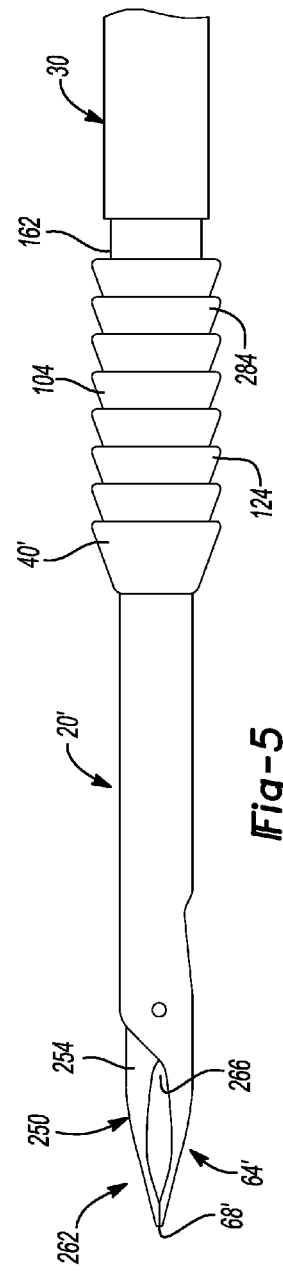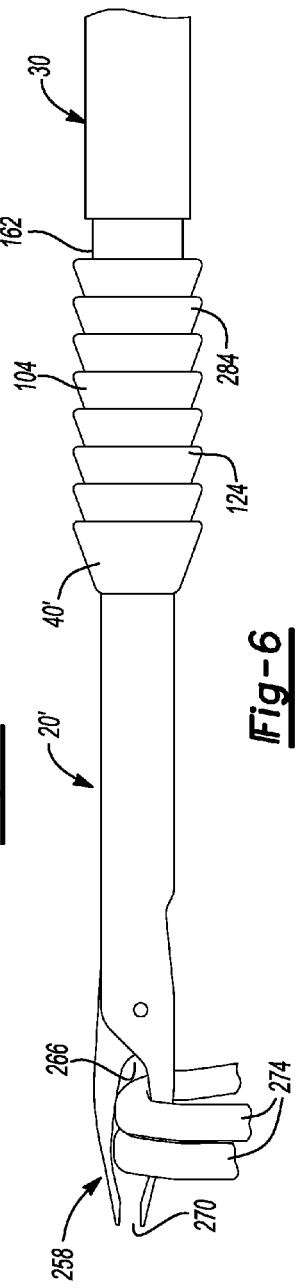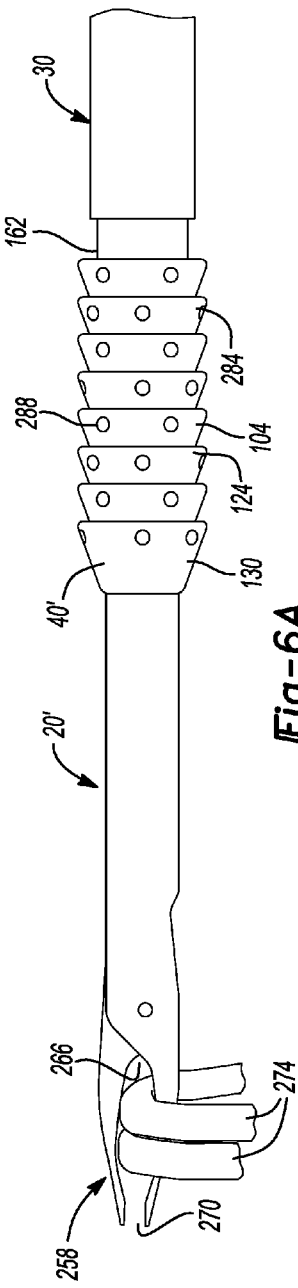

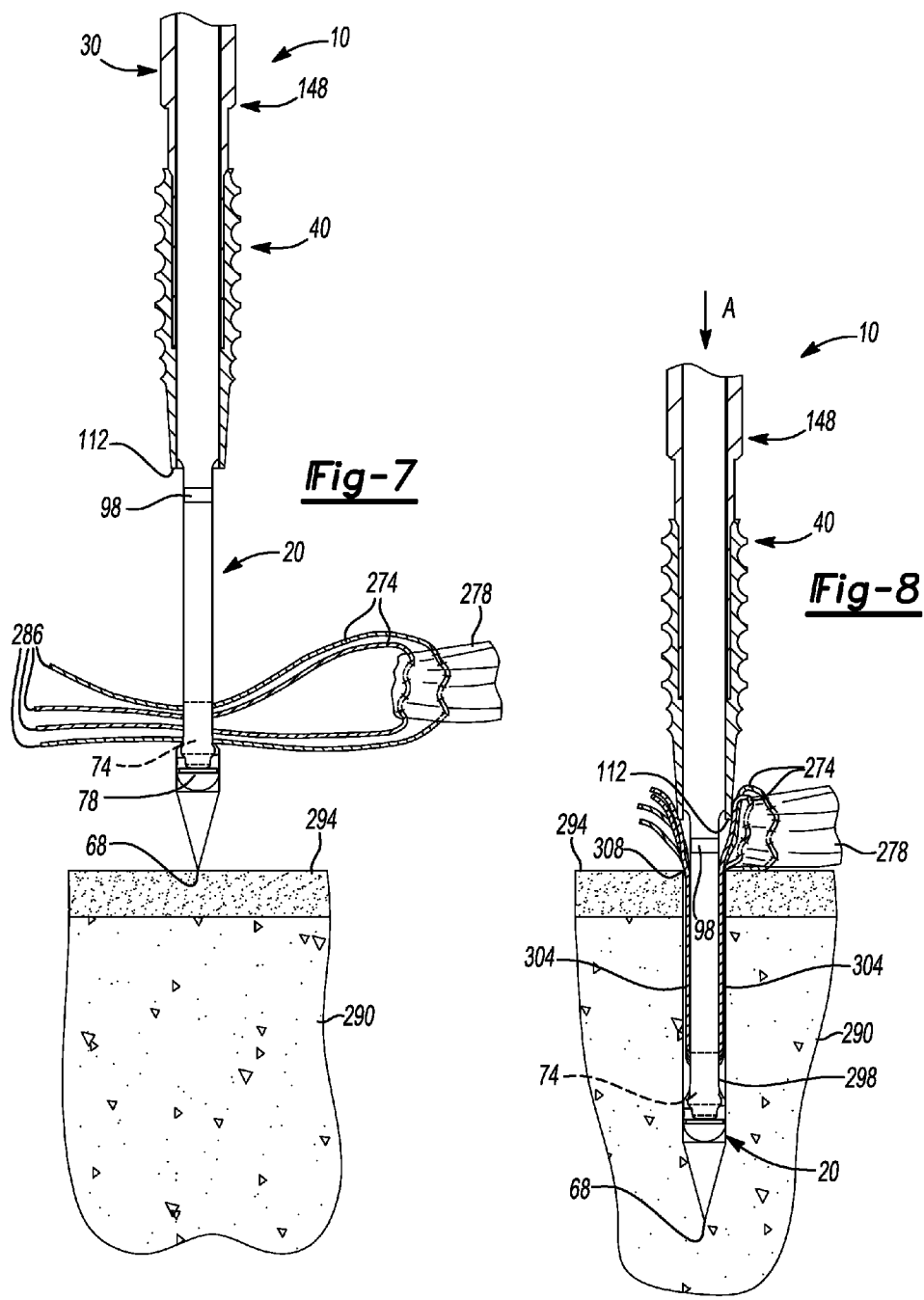

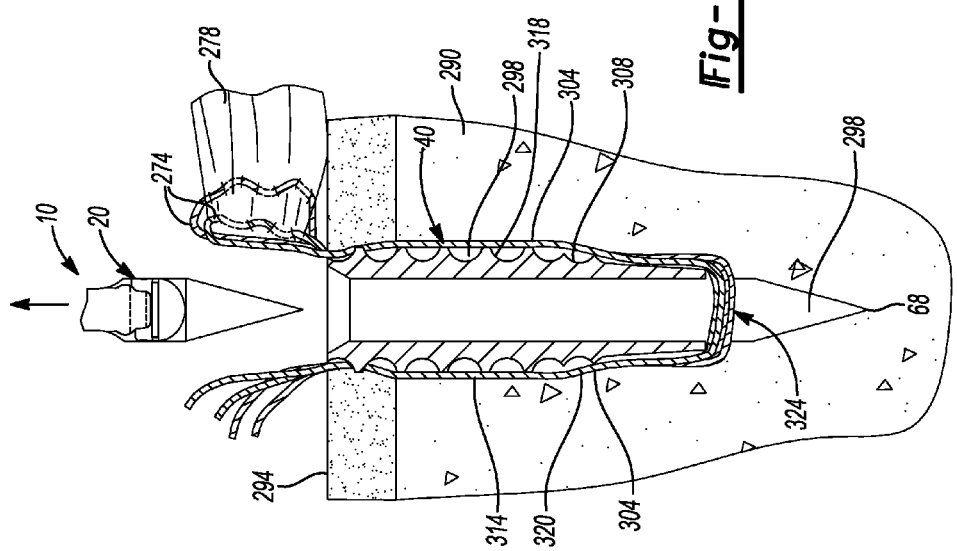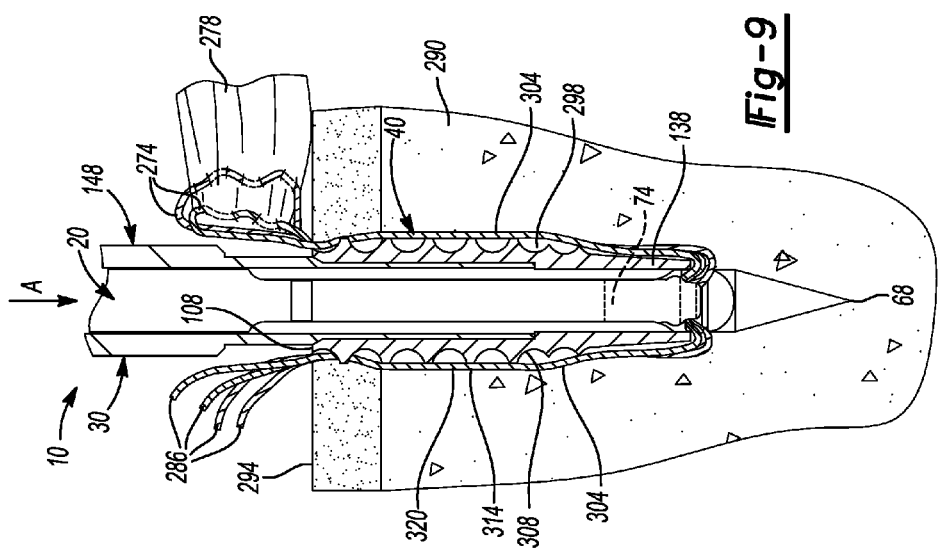

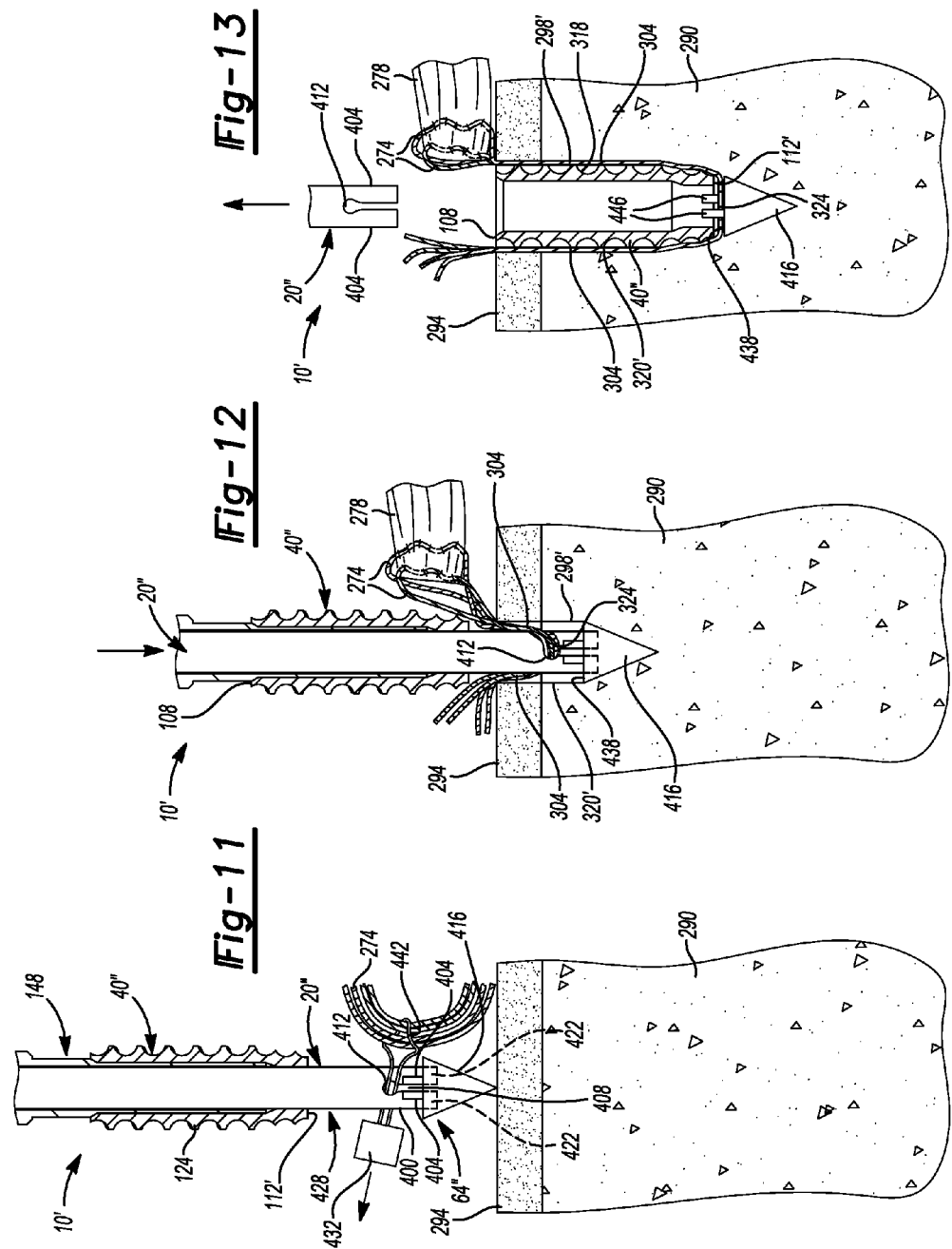

METHOD AND APPARATUS FOR COUPLING SOFT TISSUE TO BONE

CROSS-REFERENCE TO RELATED APPLICATIONS

This application claims the benefit of U.S. Provisional Application No. 61/832,344, filed on Jun. 7, 2013. The disclosure of the above application is incorporated herein by reference.

FIELD

The present disclosure relates generally to a method and apparatus for coupling a suture and/or soft tissue to bone.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Surgical or medical procedures are often performed on a body, for example, a human body or anatomy, to repair or replace various portions thereof. For example, the soft tissues of the body may need to be reattached to bones due to trauma, overuse, surgical intervention, or disease. Soft tissue can be reattached to bone using devices such as screws, staples, and various types of suture anchors. One means to fix the soft tissue to the selected area is to provide a suture through a selected portion of the soft tissue and fix the other end of the suture to a selected area on the bone using a suture anchor and a preformed hole in the bone, which can require various different instruments and tying a knot to secure the suture to the anchor. Accordingly, there is a need for improvement in the relevant art.

SUMMARY

This section provides a general summary of the disclosure, and is not a comprehensive disclosure of its full scope or all of its features.

In one form, a method for securing a suture to bone is provided in accordance with various aspects of the present disclosure. The method can include loading the suture in a distal opening of an inserter of a flexible member securing assembly. The assembly can include the inserter, a suture anchor carried by the inserter, a distal tip removably coupled to a distal end of the inserter and a driver coupled to the inserter. The suture can be positioned between the suture anchor and the distal tip in an absence of extending through the suture anchor and the distal tip. An outer surface of the bone can be pierced with the distal tip. The inserter can be advanced relative to the bone to form a pilot hole in the bone and position a distal end of the suture anchor relative to the outer surface of the bone. The distal opening, the distal tip and a portion of the suture loaded therein can be positioned in the pilot hole. The driver can be actuated to allow movement of the driver relative to the inserter. The driver can be advanced relative to the inserter in a first direction to drive the suture anchor about the inserter into the pilot hole and compress a portion of the suture between the distal end of the suture anchor and the distal tip to secure the suture anchor and the suture to the bone with an absence of a knot. The driver can be moved in a second opposite direction to remove the inserter from the pilot hole and the distal tip, suture anchor and suture.

In another form, a method for securing soft tissue to bone is provided in accordance with various aspects of the present disclosure. The method can include loading a suture in a distal opening of an inserter of a flexible member securing assembly. The suture can be coupled to soft tissue and the assembly can include the inserter, a suture anchor carried by the inserter, a distal tip removably coupled to a distal end of the inserter, and a driver coupled to the inserter. The suture anchor, inserter and driver can be concentric about a central longitudinal axis of the flexible member securing assembly and the suture can be positioned between the suture anchor and distal tip in an absence of extending through the suture anchor and the distal tip. The inserter can be advanced into a hole in the bone using the driver to position a distal end of the suture anchor relative to an outer surface of the bone. The distal opening, distal tip and a portion of the suture loaded therein can be positioned in the hole. The suture can be tensioned relative to the distal opening and the soft tissue. A lock member associated with the driver can be actuated to allow movement of the driver relative to the inserter. The driver can be advanced relative to the inserter in a first direction to drive the suture anchor about the inserter into the hole and compress the suture between the distal end of the suture anchor and the distal tip and secure the suture anchor and the suture to the bone with an absence of a knot. The driver can be moved in a second opposite direction to remove the inserter from the hole, the suture anchor and the suture.

In yet another form, a flexible member securing assembly for use in securing a flexible member relative to bone is provided in accordance with various aspects of the present disclosure. The assembly can include an inserter, a distal tip, a driver assembly and an anchor. The inserter can have a body extending along a longitudinal axis from a proximal end to a distal end. The driver assembly can include a handle and a drive member coupled to the handle. The proximal end of the inserter can be positioned in an internal bore of the drive member and handle. A lock arrangement can be associated with the driver assembly and can be configured to selectively lock the inserter to the driver assembly in one of a plurality of positions. The inserter can extend through a portion of the lock arrangement. The anchor can be slidably carried on the inserter, and the inserter, driver assembly and anchor can be concentric about the longitudinal axis. A distal opening can be formed in the inserter proximate the distal end and can be adapted to receive a flexible member and selectively retain the flexible member therein. The distal tip can be removably coupled to the distal end of the inserter such that the flexible member can be adapted to be coupled to the inserter between the distal tip and the anchor in an absence of extending through the distal tip and the anchor. The distal tip can be adapted to form a pilot hole in the bone via a force applied to the driver assembly. The driver assembly can be adapted to insert the anchor into the pilot hole about the inserter and into substantial engagement with the distal tip to secure the anchor and flexible member to the bone with an absence of a knot.

In some examples, actuating the driver can include actuating a lock arrangement to disengage a lock member from engagement with the inserter at a first position to allow axial movement of the driver relative to the inserter, where the inserter can be positioned in an internal bore of the driver. The driver can be advanced relative to the inserter in the first direction and rotated relative to the inserter to drive the suture anchor about the inserter into the pilot hole while the inserter remains positioned in the pilot hole. In various examples, the driver assembly can be configured to be advanced relative to the inserter to insert the anchor into the bone to a predetermined depth at which the lock member can automatically engage the inserter at a second position axially spaced apart from the first position to fix the driver assembly to the inserter.

In various examples, the suture can be compressed between an outer surface of the suture anchor and a wall of the pilot hole. In accordance with various aspects, moving the driver in the second opposite direction can automatically remove the distal opening from the suture. In certain examples, the suture can include a self-locking adjustable suture construct.

According to various examples, the removably coupled distal tip can capture the suture between the distal tip and the distal end of the suture anchor. In some examples, the suture can be positioned between first and second spaced apart projections axially extending from a proximal end of the distal tip.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

FIG. 2 is an enlarged view of a distal end area of the exemplary flexible member securing assembly of FIG. 1 according to various aspects of the present disclosure;

FIG. 3 is a partial sectional view of the distal end area of FIG. 2 according to various aspects of the present disclosure;

FIG. 5 is a view of an alternative exemplary inserter and rigid body for use with the exemplary flexible member securing assembly according to various aspects of the present disclosure;

FIG. 6 is a view of the inserter of FIG. 5 with a distal tip in a flexible member receiving configuration according to various aspects of the present disclosure;

FIG. 6A is a view of the inserter of FIG. 5 with an exemplary alternative rigid body according to various aspects of the present disclosure;

FIGS. 7-10 depict an exemplary method of using a flexible member securing assembly according to various aspects of the present disclosure;

FIGS. 11-13 depict an alternative exemplary inserter and rigid body and an exemplary method of using the same according to various aspects of the present disclosure;

DETAILED DESCRIPTION

The following description is merely exemplary in nature and is not intended to limit the present disclosure, its application, or uses. Although the following description is related generally to methods and apparatus for securing a flexible member to bone, it should be appreciated that the methods and apparatus discussed herein can be applicable to various bones and/or joints of the anatomy and can be utilized with various flexible members and rigid bodies or anchors.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

The present teachings provide a flexible member securing assembly and a method for using the same to secure a flexible member to bone with a rigid body and without using a knot. In an exemplary aspect, the flexible member can be a suture and the rigid body can be an anchor. In an exemplary aspect, the flexible member securing assembly can include an inserter, a driver or driver assembly and a rigid body movably coupled to each other and provided preassembled in a kit. In another exemplary aspect, the inserter can form a pilot hole in bone for receiving the rigid body while the rigid body and driver remain coupled to the inserter.

Figure 1:
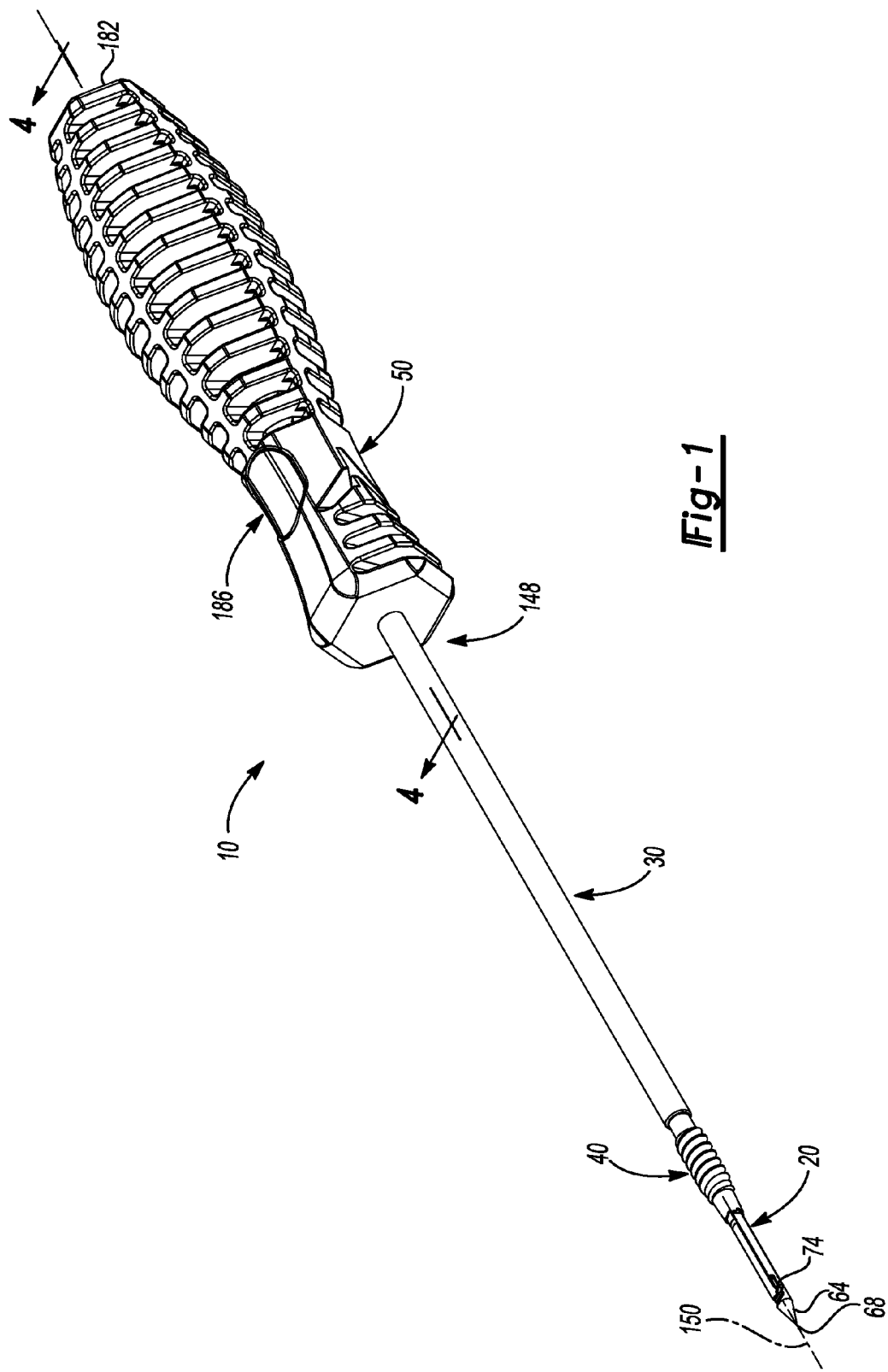
FIG. 1 is a perspective view of an exemplary flexible member securing assembly in accordance with various aspects of the present disclosure.

With initial reference to FIGS. 1-4, a flexible member securing assembly is provided and generally identified at reference numeral 10. The flexible member securing assembly 10 can include an inserter or central punch 20, a driver 30, a rigid body 40 and a handle 50. As discussed above, the flexible member securing assembly 10 can, in certain embodiments, be provided in a preassembled configuration as generally shown in FIG. 1.

The inserter 20 can include a proximal end 60 (FIG. 4) and a distal end 64. The distal end 64 can include a conical tip 68 configured to penetrate bone to form a pilot hole or bore therein, as will be discussed in greater detail below. In one exemplary implementation, the conical tip 68 can form the distal end 64. The inserter 20 can include a distal slot or eyelet 74, as generally shown in FIGS. 2-3. The distal slot 74 can include an opening 78 proximate the distal end 64 that is configured to receive one or more flexible members or sutures. In one exemplary embodiment, the opening 78 can be adjacent the conical tip 68 so as to place the sutures at a predetermined depth in the bone, as will be discussed in greater detail below. With particular reference to FIG. 2, the slot 74 can include one or more ridges or protrusions 82 and one or more valleys or recesses 86 to aid in retaining one or more flexible members therein. In the exemplary embodiment illustrated in FIG. 2, the protrusion 82 and the recess 86 can be opposed from each other.

As can also be seen in FIG. 2, the inserter 20 can include a solid body 90 extending from the proximal end 60 to the distal end 64. It should be appreciated, however, that the body 90 could also be formed in various other configurations, including hollow or cannulated. In one exemplary embodiment, the inserter can be formed as a rod or elongated cylinder. In another exemplary embodiment, the rod can include truncated sides 94 extending along a longitudinal length of inserter 20, as also shown in FIG. 2. The inserter 20 can include a depth indication 98 positioned near the distal end 64 thereof. The depth indication 98 can correspond to a predetermined position that the inserter 20 can be driven into bone before implanting the rigid body 40. In one exemplary embodiment, the depth indication 98 can be a mark or ring formed in the inserter 20. It should be appreciated, however, that the depth indication 98 can be formed in various different configurations including with or without using color as part of or the entire indication 98.

The rigid body 40 can be a suture anchor, a bone screw or other fixation device. The suture anchor 40 can include a body 104 having a proximal end 108, a distal end 112 and a throughbore 116, as generally shown in FIG. 3 with reference to FIG. 2. The suture anchor 40 can be formed of any appropriate biocompatible material including polymers, co-polymers, such as polyetheretherketone (PEEK), metals, such as titanium, and various alloys, formed from titanium, cobalt, chromium, etc. The throughbore 116 can include an internal width or diameter 120 configured to be complimentary to an external diameter or width of inserter 20 such that the inserter can be slidably received through the throughbore 116. In one exemplary implementation, the internal diameter of the throughbore 116 can be sized and shaped to provide a relatively tight or snug fit so as to prevent any unintended movement of suture anchor 40 relative to inserter 20.

The suture anchor 40 can include tissue or bone engaging features 124 positioned on an exterior 130 (FIG. 2) thereof. In the exemplary embodiment shown in FIGS. 1-4, the bone engaging features 124 can include threads, such as helical threads 128. It should be appreciated, however, that various other bone engaging features 124 may be utilized, such as ribs or protrusions. In one exemplary configuration, the suture anchor 40 can include a suture retention feature 134 at the distal end 112, as shown for example in FIG. 3. In this exemplary configuration, the suture retention feature 134 can be a recess or depression that can prevent suture strands from sliding around or off of the distal end 112.

The distal end 112 can also include a non-threaded portion 138, as shown in FIG. 3. It should be appreciated, however, that the threads 128 can alternatively extend along an entire length of the body 104. The proximal end 108 of body 104 can include a driver engaging feature 144 configured to receive a corresponding feature on a distal end of the driver 30. In the exemplary embodiment shown, the driver engaging feature 144 can include an internal hexagon pattern configured to receive an external hexagon pattern formed on the distal end of driver 30, as will be discussed in greater detail below. It should be appreciated, however, that the driver engaging feature 144 can include any male feature or female bore shape configured to receive the driver 30 and prevent relative rotational movement between the driver 30 and the suture anchor 40.

The driver 30 and handle 50 can be provided as separate components that can be coupled together by a user, or can be provided as an integral driver assembly 148. Thus, while individual components of the driver assembly 148 (i.e., driver 30 and handle 50) will be discussed below, it should be appreciated that such components can be provided in the integrated form of driver assembly 148. In one exemplary implementation, the inserter 20, driver 30, handle 50 and suture anchor 40, when assembled together, can be concentric with each other about a central longitudinal axis 150 as shown for example in FIGS. 1 and 3.

The driver 30 can include a cannulated body 154 extending from a proximal end 158 (FIG. 4) to a distal end 162, and can define a throughbore 166 extending therebetween. The distal end 162 can include a male suture anchor engaging feature 170 corresponding to the female engaging feature 144 of the suture anchor 40. In the exemplary configuration illustrated in FIGS. 1-4, the male engaging feature 170 can be a hexagon head sized and shaped to be received in the proximal end 108 of the suture anchor 40 and transmit rotational torque thereto, as will be discussed in greater detail below. The driver 30 can be received over the proximal end 60 of the inserter 20 and positioned thereon in engagement with the suture anchor 40, as generally shown in FIG. 1 with reference to FIGS. 3 and 4.

Figure 4:
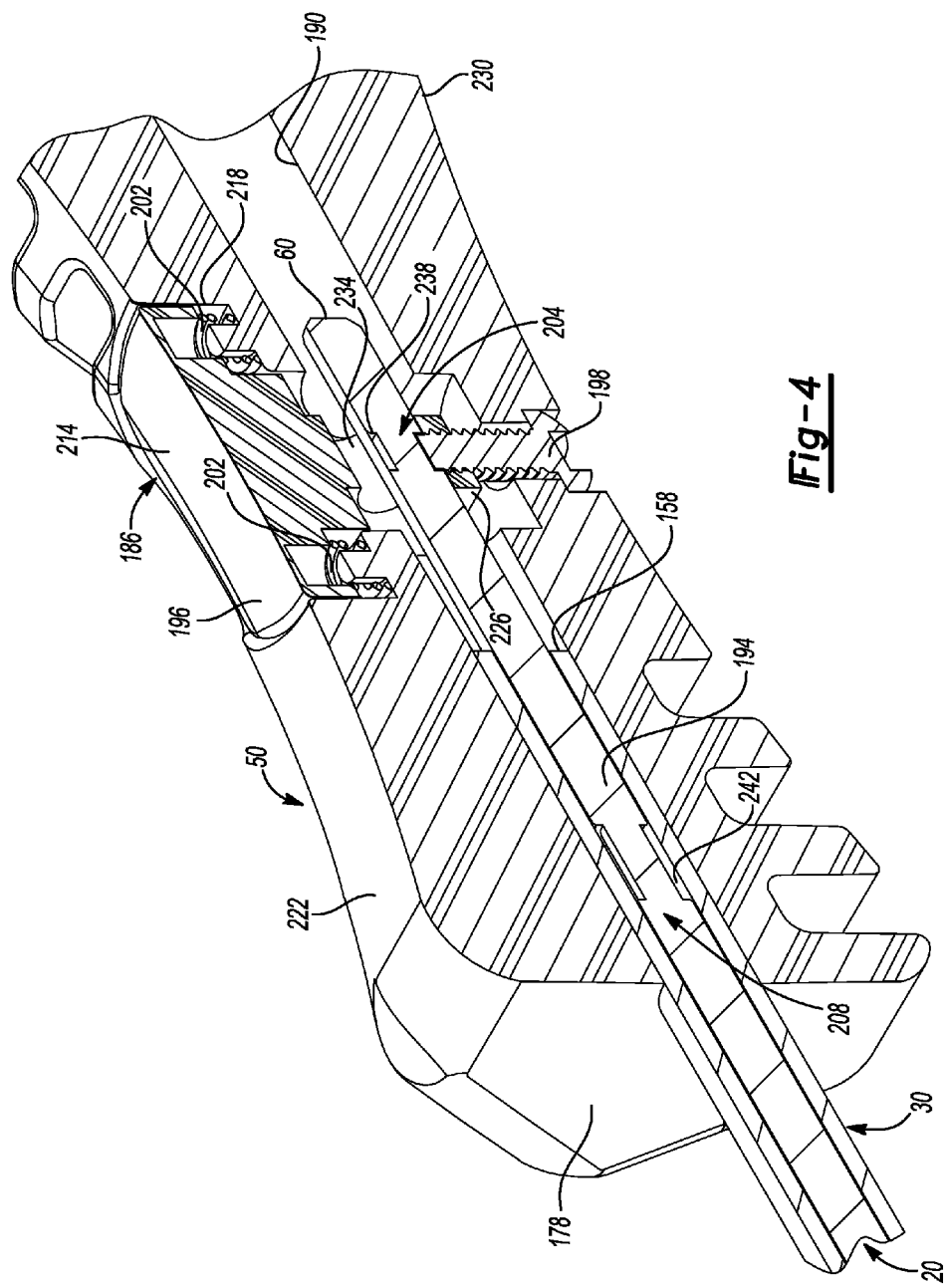
FIG. 4 is a partial sectional view of a proximal handle of the exemplary flexible member securing assembly according to various aspects of the present disclosure.

The proximal end 158 of the driver 30 can be fixed to the handle 50, as generally shown in FIG. 4. The handle 50 can be used to grasp and manipulate (e.g., cause movement of) the flexible member securing assembly 10. The handle 50 can include a proximal end 178, a distal end 182 (FIG. 1), a locking arrangement 186, and can define a throughbore 190. The handle 50 can be fixedly coupled to the driver 30, as discussed above and shown in FIG. 4. The handle 50 and driver 30 (driver assembly 148) can be slidably positioned over the proximal end 60 of the inserter 20 such that a proximal portion 194 of the inserter 20 adjacent the proximal end 60 thereof extends beyond the proximal end of driver 30 and at least partially into the throughbore 190, as also shown in FIG. 4.

The locking arrangement 186 can include an actuator 196, a lock member 198, and an optional biasing member 202. The locking arrangement 186 can be configured to selectively engage the handle 50 (and thus the driver 30) to the inserter 20 in one of a plurality of positions. In one exemplary embodiment, the locking arrangement 186 can be configured to axially fix the driver assembly 148 to the inserter 20 in a first position 204 such that a force applied to the handle 50 causes movement of the driver assembly 148 and inserter 20 as a combined unit. Upon actuation of the locking arrangement 186 to release the handle 50 from engagement with the inserter 20 at the first position 204, the driver assembly 148 can slide axially relative to the inserter 20 to move the suture anchor 40 relative to the inserter 20, as will be discussed in greater detail below. In one exemplary embodiment, the locking arrangement 186 can be configured to automatically reengage the inserter 20 at a second position 208 to again axially fix the driver assembly 148 to the inserter 20.

In the exemplary embodiment shown in FIG. 4, the actuator 196 can include a button or other depressible member 214 positioned in a cavity 218 formed on a first side 222 of handle 50. The button 214 can include a shaft or projection 226 extending therefrom and toward a second opposed side 230 of handle 50. The projection 226 can include a cut-out or clearance 234 configured to allow the inserter 20 to move relative thereto, as shown in FIG. 4. The projection 226 can be coupled to the lock member 198, which can be selectively coupled to a first retention feature or depression 238 in inserter 20 that forms the first position 204. Depression of the button 214 into cavity 218 can move the lock member 198 out of first depression 238 thereby selectively disengaging lock member 198 from inserter 20. It should be appreciated that while the flexible member securing assembly 10 has been discussed as including the locking arrangement 186, the securing assembly 10 can include various different locking arrangements, such as a key slot arrangement, that are configured to selectively lock the driver assembly 148 to the inserter 20.

As discussed above, a biasing member, such as a spring or other elastic member 202, can bias the button 214 to a non-depressed position which, in turn, can bias the lock member 198 into engagement with inserter 20. Upon disengagement of the lock member 198 from the first position 204 of inserter 20 in the manner discussed above, the driver assembly 148 can be axially advanced relative to the inserter 20 in a direction toward the distal end 64 of inserter 20. The button 214 can then be released thereby providing for the biasing member 202 to bias the lock member 198 into sliding engagement with the body 90 of inserter 20. While the lock member 198 is slidably engaged with the body 90 of inserter 20, the handle 50 can be rotationally and/or axially advanced relative to the inserter 20 until the lock member 198 aligns with a second retention feature or depression 242 that forms the second position 208. Upon such alignment, the biasing member 202 can automatically move the lock member 198 into engagement with the second depression 242 thereby again selectively fixing the handle 50 and driver 30 (driver assembly 148) to the inserter 20.

With additional reference to FIGS. 5 and 6 and continuing reference to FIGS. 1-4, an alternative exemplary inserter 20' is shown having an alternative distal end 64'. The alternative inserter 20' can be utilized with assembly 10 in place of inserter 20 or with a different assembly. In the exemplary embodiment illustrated, the alternative distal end 64' can include a movable eyelet configuration 250 for selectively receiving one or more flexible members, such as sutures, and for forming the pilot bore in the bone. The moveable eyelet configuration 250 can include one or more movable jaws 254 that can be selectively positioned in an open position 258 and a closed position 262. The closed position 262 (FIG. 5) can form an enclosed distal eyelet 266, as well as a conical distal tip 68' for use in forming the pilot bore in the bone.

With particular reference to FIG. 6, one or more of the jaws 254 can be moved to the open position 258 to thereby create an opening 270 for loading one or more sutures 274 in the distal eyelet 266. The eyelet 266 can be sized and shaped such that when the movable jaws 254 are in the closed position 262, the one or more sutures 274 can slide relative to distal eyelet 266. The one or more movable jaws 254 can provide for arthroscopic loading of the one or more sutures 274 in the distal eyelet 266. The conical distal tip 68' can be used to pierce the bone and form a bore therein, as will be discussed below in greater detail.

With continuing reference to FIGS. 5-6A, an alternative suture anchor 40' is shown slidably coupled to inserter 20' in the same manner as discussed above for suture anchor 40 and inserter 20. Suture anchor 40' can be similar to suture anchor 40 such that only differences will be discussed below in detail. Suture anchor 40' can include bone engaging features 124 in the form of external ribs or protrusions 284. Suture anchor 40' can also include one or more openings or fenestrations 288 defined by the cannulated body 104, as shown for example in FIG. 6A. In one exemplary configuration, suture anchor 40' can include a plurality of fenestrations 288 extending through body 104 from the exterior 130 to the throughbore 116. The fenestrations 288 can be provided in various dimensions and/or geometries and can promote healing and in-growth of bone. The fenestrations 288 can also decrease a mass of the suture anchor 40', which can also serve to promote healing. It should be appreciated that while fenestrations 288 are shown in association with suture anchor 40' in FIG. 6A, the fenestrations 288 can be provided with any of the various suture anchors discussed herein.

Suture anchor 40' can be axially driven or punched into the bone by driver 30 as opposed to being threaded into the bone. In this regard, the distal end 162 of driver 30 can include the same male engaging feature as used with suture anchor 40, or can include an alternative male engaging feature as rotational torque is not required for suture anchor 40'. Likewise, the proximal end of suture anchor 40' can include the same female engaging feature 144 as suture anchor 40, or an alternative engaging feature corresponding to the alternative engaging feature of driver 30. In one exemplary embodiment, the alternative male engaging feature can be a reduced diameter portion forming an external shoulder, and the alternative female engaging feature can be an annular recess forming an internal shoulder. It should be appreciated that the suture anchors 40, 40' can be used with either inserter configuration 20, 20' discussed herein.

With additional reference to FIGS. 7-10 and continuing reference to FIGS. 1-6, an exemplary method for securing soft tissue to bone with flexible member securing assembly 10 will now be discussed. It should be appreciated that while the discussion will continue with reference to flexible member securing assembly 10 having inserter 20 and suture anchor 40, the alternative suture anchor 40' and/or alternative inserter 20' could also be utilized to secure the sutures and soft tissue to bone without a knot.

With particular reference to FIG. 7, one or more sutures 274 coupled to soft tissue 278 can be loaded onto inserter 20 of the flexible member securing assembly 10. It should be appreciated that the sutures 274 can be loaded onto the inserter 20 in an assembled configuration, as shown in FIG. 1, or onto an individual inserter 20 which can then be slidably coupled to the driver assembly 148. The discussion will continue, however, with reference to use of the assembly 10 in the preassembled configuration.

In the exemplary configuration illustrated, two looped suture strands 274 can be positioned in slot 74 of inserter 20 such that free ends 286 extend beyond slot 74 a distance greater than a longitudinal length of anchor 40. It should be appreciated, however, that the free ends 286 could extend from slot 74 more or less than discussed above. It should also be appreciated that various other suture configurations could be coupled to slot 74 and/or the soft tissue 278, including various knotless self-locking adjustable suture constructs, an example of which will be discussed herein.

With the desired suture strands loaded onto inserter 20, the distal tip 68 can be positioned at a desired suture retention location of a bone 290, as shown for example in FIG. 7. The driver 30 can be selectively fixed to the inserter 20 at the first position 204, as discussed above and shown in FIG. 3. A force can then be applied to the flexible member securing assembly 10, such as an axial force in the direction of arrow A, to punch or drive the distal tip 68 of inserter 20 into bone 290, as shown for example in FIG. 8. Once the distal tip 68 pierces an outer surface 294 of the bone 290, the securing assembly 10 can be further driven in the direction of arrow A to form a pilot hole 298 in bone 290 for receipt of suture anchor 40.

In the exemplary configuration illustrated in the various figures, the axial force can be applied to the proximal end of handle 50 of driver assembly 148, which can be selectively fixed to inserter 20. The inserter 20 can be driven via driver assembly 148 until the depth indication 98 is roughly in line with the outer surface 294 of bone 290, as also shown in FIG. 8. When the inserter 20 is in this position, the slot or eyelet 74 can be positioned at a predetermined depth below the outer surface 294 of the bone 290 such that the opening of the eyelet 74 is below a depth for driving the suture anchor 40 below the outer surface 294 of the bone 290. First and second portions 304 of the suture strands 274 can extend from the eyelet 74 out of the formed pilot hole 298, as also shown in FIG. 8. It should be appreciated, however, that the hole 298 could alternatively be pre-drilled.

As discussed above, the suture strands 274 can be slidably positioned in eyelet 74 such that the free ends 286 can be tensioned to draw the soft tissue 278 to a desired position relative to the formed pilot hole 298. In the example illustrated, the free ends 286 can be tensioned to draw the soft tissue 278 to a position adjacent an opening 308 of pilot hole 298 while the distal tip 68 of inserter 20 is positioned in pilot hole 298. With the sutures 274 tensioned as discussed above, an axial force can again be applied to handle 50 to punch the distal end 112 of suture anchor 40 slightly into bone 290. In one exemplary configuration, the non-threaded portion 138 of suture anchor 40 can be driven into bone 290 via an axial force imparted onto handle 50.

The actuator button 214 of handle 50 can then be depressed in the manner discussed above to release driver assembly 148 from being selectively fixedly coupled to inserter 20. A rotational force can be applied to handle 50 to rotate driver 30 about inserter 20 and thread suture anchor 40 into bone 290. In other words, inserter 20 can remain stationary or positioned in bone 290 while suture anchor 40 is threaded into pilot hole 298 to a predetermined depth. In this regard, inserter 20 can serve as a guide for threading suture anchor 40 into bone 290. It should be appreciated, however, that the actuator button 214 can be depressed after tensioning the sutures 274 and before applying the axial force to the handle 50 to punch the distal end 112 of suture anchor 40 slightly into bone 290.

Suture anchor 40 can include a larger outer diameter than an inner diameter of pilot hole 298 such that a threaded interference fit 314 is created between the bone 290 and suture anchor 40 as the anchor is threaded into pilot hole 298 about inserter 20. The first and second suture portions 304 can be positioned between an outer surface 318 of the suture anchor 40 and an inner wall 320 of the pilot hole 298 such that the threaded interference fit 314 secures the suture strands 274 and thus the soft tissue 278 coupled thereto to bone 290 without requiring a knot or additional suture tying device. In one exemplary implementation, the suture portions 304 can be compressed between the outer surface 318 of suture anchor 40 and the inner wall 320 of pilot hole 298.

As discussed above, the suture anchor 40 can be threaded into pilot hole 298 of bone 290 to a predetermined depth to lock the sutures 274 to bone 290. In one exemplary configuration, the predetermined depth can be a depth at which the proximal end 108 of suture anchor 40 is flush or substantially flush with the outer surface 294 of bone 290 or below the outer surface 294 of bone 290. In an exemplary configuration, the predetermined depth can be coordinated with the second position 208 of inserter 20. In this configuration, when the predetermined depth is reached, the lock member 198 can align with the second position 208. Upon such alignment, the biasing member 202 can automatically urge the lock member 198 into engagement with the second depression 242 thereby preventing further advancement of the driver 30 (and thus suture anchor 40) relative to inserter 20.

Once suture anchor is threaded to the predetermined depth, such as in the manner discussed above, the inserter 20, driver 30 and handle 50 can be removed simultaneously. In particular, since the driver assembly 148 can be selectively fixed to the inserter 20 at the second position 208, the handle 50 can be moved in a direction opposite of arrow A to slide the inserter 20 and driver assembly 148 out of pilot hole 298 and relative to suture anchor 40, as shown for example in FIG. 10. A looped end 324 of the suture strands 274 can slide out of slot 74 via opening 78 as the inserter 20 and driver assembly 148 are removed simultaneously as a unit. It should be appreciated that while flexible member securing assembly 10 is discussed above in connection with forming pilot hole 298, the assembly could also be used with a preformed hole 298.

Turning now to FIGS. 11-13, an alternative flexible member securing assembly 10' will now be discussed. Flexible member securing assembly 10' can be similar to flexible member securing assembly 10 such that only differences will be discussed in detail and like reference numerals can refer to like or similar components and/or features. The flexible member securing assembly 10' can include an inserter 20" having an alternative distal end 64". The alternative distal end 64" can include a forked end 400 having first and second spaced apart members 404 forming a channel 408 terminating in or forming a distal eyelet 412. An anchor body in the form of a conical tip 416 can be removably secured to the distal end 64", which can form a selective closure of eyelet 412. In one exemplary configuration, the first and second members 404 can be received in correspondingly sized and shaped bores 422 in conical tip 416, as shown for example in FIG. 11. The bores 422 can, in one exemplary configuration, be sized and shaped to create a slight interference fit with first and second members 404 to releasably retain conical tip 416 on inserter 20".

The flexible member securing assembly 10' can be provided in a preassembled configuration and as part of a kit, similar to assembly 10. In this regard, the assembly 10' can include a suture anchor 40", a punch or inserter assembly 428 that includes inserter 20" with conical tip 416 preassembled thereto, the driver assembly 148, and a suture passer, such as a Nitinol kite 432, prepositioned through distal eyelet 412.

The suture anchor 40" can be any suitable suture anchor having bone engaging external features 124 and a distal end configured to mate with a proximal end 438 of conical tip 416. In the exemplary configuration illustrated, suture anchor 40" can be similar to suture anchor 40 without the non-threaded portion 138, as shown for example in FIG. 11.

In operation, one or more suture strands 274 can be positioned through a capture loop 442 of suture passer 432, which can be coupled to the flexible member securing assembly 10'. The suture passer 432 can then be used to pull a portion of the suture strands 274 through distal eyelet 412 such that, for example, the free ends are pulled through distal eyelet 412, as shown for example in FIG. 13 with reference to FIG. 12.

The flexible member securing assembly 10' can be positioned at a desired bone location for securing suture anchor 40" in a similar manner as discussed above for assembly 10. An axial force can be applied to the driver assembly 148, such as at the proximal end thereof, to drive the distal end of inserter assembly 428 into the bone 290. In particular, in the exemplary embodiment illustrated, the distal eyelet 412 with the loaded suture strands 274 and the conical tip 416 can be punched into the bone 290 to form a bone hole 298'. Similar to assembly 10 discussed above, first and second portions 304 of the suture strands 274 can extend from the distal eyelet 412 out of the bone hole 298'.

Once the punch assembly 428 is inserted into the bone 290 to a predetermined depth, such as a depth sufficient to place the proximal end 108 of suture anchor 40" flush with or below the outer surface 294 of bone 290, the suture anchor 40" can be threaded into the bone 290 about inserter 20". In one exemplary embodiment, the driver assembly 148 can be used to thread suture anchor 40" into bone 290 in a similar manner as discussed above for suture anchor 40.

With additional reference to FIG. 13, the suture anchor 40" can be threaded into bone 290 until a distal end 112' engages the proximal end 438 of conical tip 416. With this action, the first and second portions 304 of suture strands 274 can be compressed between the outer surface 318 of suture anchor 40" and an inner wall 320' of formed bone hole 298', as can be seen in FIG. 13. In one exemplary configuration, the looped end 324 of suture strands 274 can be engaged by the distal end 112' of suture anchor 40" as the anchor is being inserted toward conical tip 416. This action can automatically remove the looped ends 324 from the distal eyelet 412 of inserter 20" and place the looped ends 324 in engagement with the proximal end 438 of conical tip 416. Depending on the insertion depth of the suture anchor 40", the looped ends 324 can be compressed between the distal end 112' of anchor 40" and the proximal end 438 of conical tip 416. It should be appreciated that, in certain embodiments, a portion of the looped end 324 may remain in the distal eyelet 412 and/or channel 408 until the inserter 20" is removed from bone 290, as will be discussed below.

In the exemplary configuration shown in FIG. 13, conical tip 416 can include two spaced apart projections 446 extending axially from the proximal end 438. In this configuration, the looped ends 324 and/or another portion of the suture strands 274 can be positioned between the projections 446 to aid in preventing the suture strands 274 from sliding around the conical tip 416. Once the suture anchor 40" is inserted to the appropriate depth, such as the proximal end thereof being flush with or substantially flush with or below the outer surface 294 of bone 290, the inserter 20" and driver assembly 148 can be simultaneously removed from bone 290. As can be seen in FIG. 13, the suture anchor 40" and conical tip 416 can remain implanted in bone 290 thereby securing the suture strands 274 to bone 290 without requiring a knot.

Figure 14:
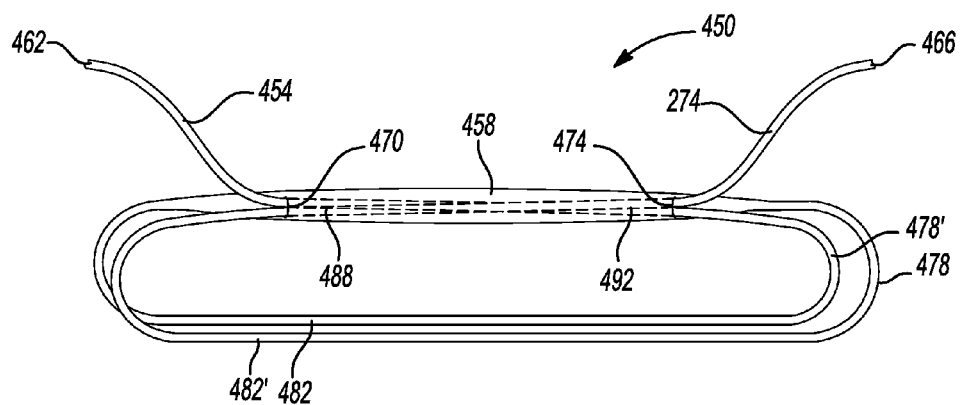
FIG. 14 depicts an exemplary flexible member construct according to various aspects of the present disclosure.
Figure 15:
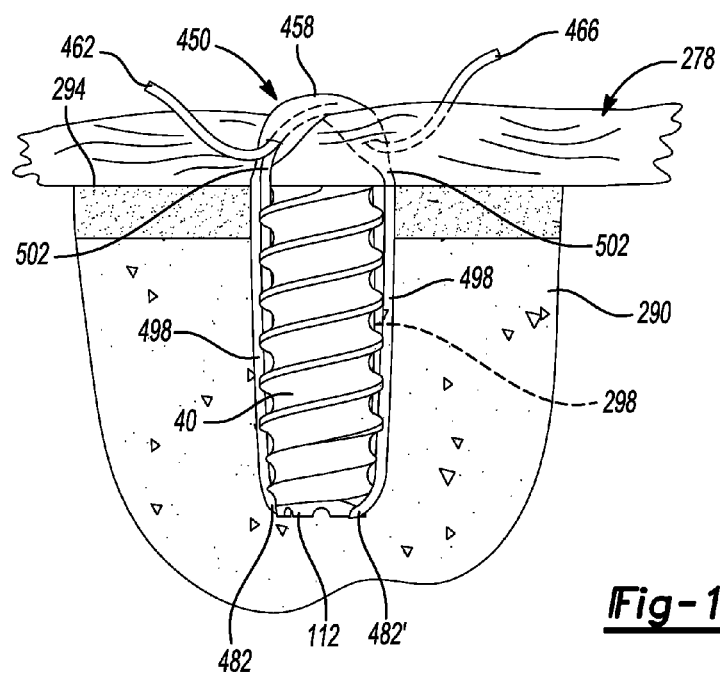
FIG. 15 depicts an exemplary method of using the exemplary flexible member construct along with an exemplary rigid body according to various aspects of the present disclosure.

Turning now to FIGS. 14-15, an alternative suture configuration is provided and, in one exemplary implementation, can be used with the various flexible member securing assemblies discussed herein. The suture configuration can be in the form of a knotless, adjustable self-locking suture construct 450 shown in FIG. 14. As will be discussed below, free ends of suture construct 450 can be tensioned to reduce a size of the adjustable loops and can automatically maintain the reduced size without requiring a knot. Suture construct 450 can be used, for example, to compress a fractured or sectioned bone, to couple and/or tension portions of the anatomy, and/or to secure soft tissue to bone.

As shown in FIG. 14, suture construct 450 can be formed from suture 274 which, in this exemplary implementation, can be a hollow or braided or multiple-filament braided suture having a hollow core. In various aspects, the suture 274 can define a substantially tubular hollow shape. Suture construct 450 can be formed to include a double loop configuration having two loops that each traverse a path from one end of a passage portion to the other end thereof, as will be discussed below. Suture construct 450 can include a body 454 that defines a longitudinal passage portion 458 therein between first and second ends 462, 466. The passage portion 458 can define a pair of apertures 470, 474 at opposed ends thereof.

Suture construct 450 can be formed by passing first end 462 through aperture 474, through passage portion 458 and out aperture 470. The second end 466 can be passed through aperture 470, through the passage portion 458 and out the aperture 474. In various aspects, the first and second apertures 470, 474 can be formed during the braiding process as loose portions between pairs of fibers defining the suture 274. Passing ends 462, 466 through the apertures 470, 474 can form adjustable loops 478, 478'. The adjustable loops 478, 478' can define mount or summit portions 482, 482' of the suture construct 450 and can be disposed generally opposite from the passage portion 458.

The longitudinal and parallel placement of the first and second ends 462, 466 of suture 274 within the passage portion 458 resists the reverse relative movement of first and second portions 488, 492 of the suture construct 450 once it is tightened. The tensioning of the ends 462, 466 can cause relative translation of the portions 488, 492 relative to passage portion 458. Upon applying tension to the first and second ends 462, 466, the loops 478, 478' can be reduced to a desired size or placed in a desired tension. Tension in the loops 478, 478' can cause the body of suture 274 defining the passage portion 458 to be placed in tension and therefore cause passage portion 458 to constrict about the portions 488, 492. This constriction can cause the adjustable suture construct 450 to "automatically" lock in a reduced size or smaller diameter configuration under tension without requiring a knot.

With additional reference to FIG. 15 and reference back to FIGS. 1-10, suture construct 450 is shown in an exemplary procedure for securing soft tissue 278 to bone 290. Suture construct 450 can be used in a similar procedure as discussed above for flexible member securing assembly 10. In one exemplary procedure, the summit portions 482, 482' can be coupled to slot 74 of inserter 20 in a similar manner as discussed above for suture strands 274. It should be appreciated that while the discussion will continue with reference to flexible member securing assembly 10 and inserter 20, the suture construct 450 and this procedure could also be implemented with the various other inserters and/or securing assemblies discussed herein.

With the summit portions 482, 482' coupled to inserter 20, the suture anchor 40 can be implanted in the same or a similar manner as discussed above in FIGS. 7-10, where the passage portion 458 and free ends 462, 466 can extend from hole 298. As can be seen in FIG. 15, the summit portions 482, 482' can be positioned adjacent to or engage the distal end 112 of suture anchor 40 and portions 498 extending therefrom can be compressed between anchor 40 and bone 290. Soft tissue 278 can be positioned under passage portion 458 so as to be between passage portion 458 and the outer surface 294 of bone 290. In other words, passage portion 458 and portions 502 of suture construct 450 extending from hole 298 can encircle soft tissue 278 relative to bone 290. The free ends 462, 466 of suture construct 450 can be tensioned to reduce a size of loops 478, 478' to secure soft tissue 278 to bone 290 under tension and maintain such tension without use of a knot. In one exemplary implementation, the free ends 462, 466 can be tensioned after driving inserter 20 into bone 290 to the predetermined depth with summit portions 482, 482' coupled thereto and before implanting suture anchor 40.

Figure 16:
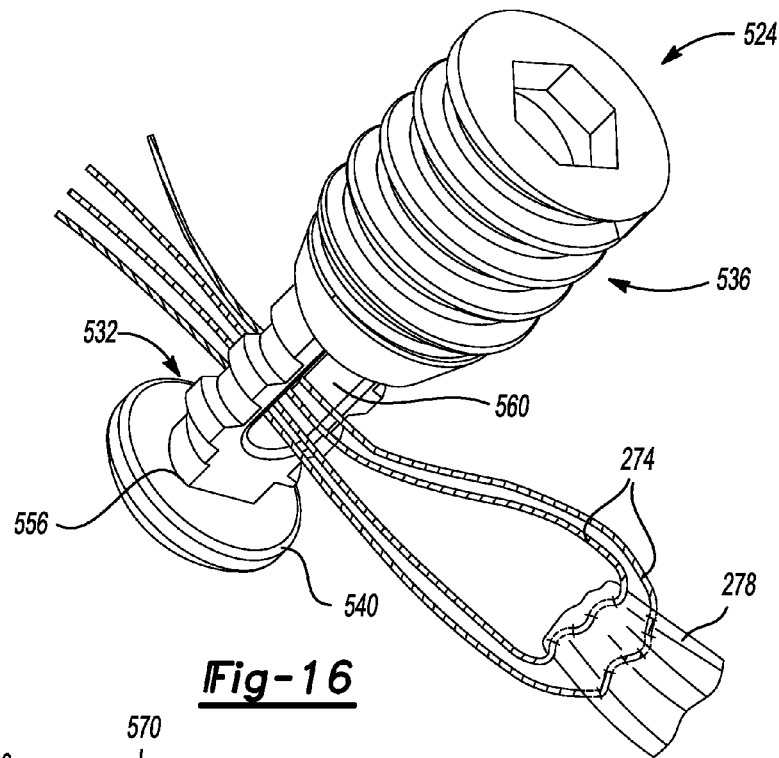
FIGS. 16 and 17 are views of an exemplary alternative rigid body assembly and associated inserter assembly according to various aspects of the present disclosure.
Figure 17:
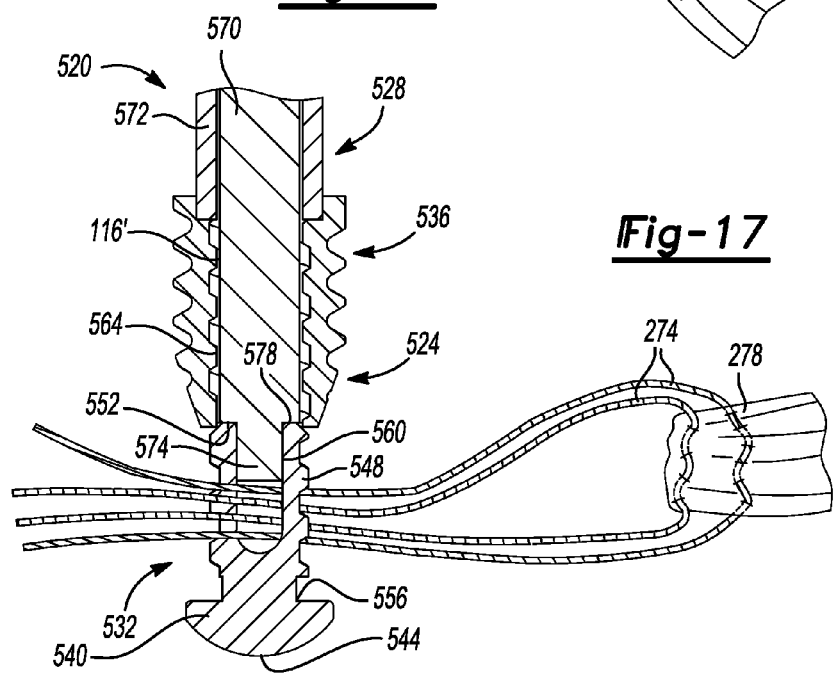

Turning now to FIGS. 16-17, another exemplary flexible member securing assembly 520 is shown in accordance with various aspects of the present teachings. Flexible member securing assembly 520 can include an anchor assembly 524 and a driver assembly 528. Anchor assembly 524 can include a first or distal body member 532 and a second or proximal body member 536.

First body member 532 can include lower portion 540 forming a distal end 544 and an upper portion 548 extending from the lower portion 540 and forming a proximal end 552. The distal end 544 can be in the form of a rounded or arcuate distal tip having a width or diameter larger than a width or diameter of the upper portion 548 so as to form a shoulder 556. Upper portion 548 can include external threads and a blind channel 560 having an opening at the proximal end 552. The second body member 536 can be similar to or substantially similar to suture anchor 40" with the inclusion of internal threads 564 and will not be discussed in greater detail herein.

The driver assembly 528 can include a first shaft member 570 and a second shaft member 572. First shaft member 570 can be coaxially received in and slidable relative to second shaft member 572. First shaft member 570 can be sized and shaped to be received in throughbore 116' and can include a distal projection 574 sized and shaped to fit in channel 560. Distal projection 574 can form a shoulder 578 with shaft member 570, which can engage the proximal end 552 of upper portion 548, as shown in FIG. 17.

The second shaft member 572 can include a larger outer width or diameter than first shaft member 570 and can include a male coupling feature configured to engage a female coupling feature in the proximal end of second body member 536. In one exemplary configuration, the male and female coupling features include corresponding hexagonal patterns such that the second shaft member 572 can rotate second body member 536 relative to first body member 532, as will be discussed in greater detail below.

In operation, the flexible member securing assembly 520 can be provided as a kit with the anchor assembly 524 preassembled to the driver assembly 528, as generally shown in FIG. 17 (except that the lower portion 540 would be threadably engaged to the upper portion 548). In this configuration, the components of the flexible member securing assembly 520 can be concentric with each other.

Suture strands 274 or other flexible members can be positioned in channel 560, as generally shown in FIG. 16. The first body member 532 can be inserted into a formed hole in bone 290 and then the suture strands 274 can be tensioned. The second shaft member 572 can be rotated to thread the second body member 536 about the first body member 532 and into the formed hole. The first shaft member 570 can prevent the first body member 532 from rotating. This action can thread second body member 536 about the upper portion 548 of first body member 532 until a distal end of the second body member 536 engages the shoulder 556. Upon engagement of the second body member 536 with the shoulder 556, the second body member 536 can be threaded into the bone hole to a predetermined depth.

At this point of the procedure, the suture strands 274 can be pinched or compressed between the distal end of the second body member 536 and the shoulder 556 of first body member 532, as well as between the outer threaded surface of the second body member 536 and the wall of the bone hole thereby securing the suture strands 274 to bone without requiring a knot or additional securing device or procedure. The driver assembly 528 can then be slidably removed from the implanted anchor assembly 524.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A method for securing a suture to bone, comprising:
   loading the suture in a slot of an openable eyelet, wherein the slot includes an opening proximate a distal end of an inserter of a flexible member securing assembly, the assembly including the inserter, a suture anchor carried by the inserter, a distal tip removably coupled to a distal end of the inserter and a driver coupled to the inserter, the suture being positioned between the suture anchor and the distal tip within the slot while extending neither through the suture anchor nor the distal tip, a combination of the slot and the distal tip forming the openable eyelet;
   piercing an outer surface of the bone with the distal tip;
   advancing the inserter relative to the bone to form a pilot hole in the bone and position a distal end of the suture anchor relative to the outer surface of the bone, the distal tip, the opening of the slot and a portion of the suture loaded therein being positioned in the pilot hole;
   actuating the driver to allow movement of the driver relative to the inserter;
   advancing the driver relative to the inserter in a first direction to drive the suture anchor about the inserter into the pilot hole and compress a portion of the suture between the distal end of the suture anchor and the distal tip and secure the suture anchor and the suture to the bone without forming a knot in the suture; and
   moving the driver in a second direction opposite the first direction to remove the inserter from the pilot hole and the distal tip, suture anchor and suture, the moving step uncoupling the distal tip from the inserter, opening the openable eyelet, and causing the suture to move through the opening of the slot of the openable eyelet as the inserter is removed from the pilot hole.

2. The method of claim 1, wherein the suture is coupled to soft tissue, and wherein piercing the outer surface of the bone with the distal tip includes piercing the outer surface of the bone with the distal tip while the inserter is coupled to the suture, the suture anchor, the distal tip and the driver.

3. The method of claim 1, wherein actuating the driver includes actuating a lock arrangement associated with a handle of the driver to allow axial movement of the driver relative to the inserter, the inserter being positioned in an internal bore of the driver.

4. The method of claim 3, wherein actuating the lock arrangement includes moving a depressible member to disengage a lock member from engagement with a first retention area of the inserter, wherein the inserter extends through a cavity of the depressible member.

5. The method of claim 4, wherein actuating the lock arrangement includes the moving the depressible member to disengage the lock member that is biased into engagement with the first retention area such that upon axial movement of the inserter and release of the depressible member, the lock member reengages the inserter at a position different than the first retention area.

6. The method of claim 5, wherein advancing the driver relative to the inserter in the first direction includes advancing the driver in the first direction until the lock member engages a second retention area of the inserter axially spaced apart from the first retention area, the second retention area corresponding to a proximal end of the suture anchor being at a predetermined position relative to the outer surface of the bone.

7. The method of claim 3, wherein advancing the driver relative to the inserter in the first direction to drive the suture anchor about the inserter into the pilot hole includes axially advancing and rotating the driver relative to the inserter to thread the suture anchor into the pilot hole about the inserter while the inserter remains positioned in the pilot hole.

8. The method of claim 3, wherein advancing the driver to secure the suture anchor and the suture to the bone without forming a knot in the suture includes compressing the suture between an outer surface of the suture anchor and a wall of the pilot hole in the bone.

9. The method of claim 1, wherein moving the driver in the second opposite direction automatically removes the slot from the suture and the inserter from the distal tip.

10. The method of claim 9, wherein the distal tip includes a pointed distal tip having a larger width than a width of the inserter.

11. The method of claim 10, wherein advancing the driver relative to the inserter in the first direction to drive the suture anchor about the inserter into the pilot hole includes inserting the suture anchor into the pilot hole to place a distal end of the suture anchor into engagement with the removably coupled distal tip, wherein a portion of the suture is compressed between the distal end of the suture anchor and the removably coupled distal tip.

12. The method of claim 1, wherein advancing the driver relative to the inserter in a first direction to drive the suture anchor about the inserter into the pilot hole and compress a portion of the suture between the distal end of the suture anchor and the distal tip includes positioning the suture between first and second projections extending from a proximal end of the distal tip.

13. The method of claim 12, wherein the first and second projections are spaced apart and orientated relative to the slot such that the suture can be moved by the suture anchor relative to the slot and into a space between the first and second projections such that the suture can be positioned between the first and second projections by the suture anchor while the distal tip is removably coupled to the inserter.

14. The method of claim 1, wherein the suture includes a self-locking adjustable suture construct.

15. A method for securing soft tissue to bone, comprising:
loading a suture in a slot of an openable eyelet, wherein the slot includes an opening proximate a distal end of an inserter of a flexible member securing assembly, the suture being coupled to soft tissue, the assembly including the inserter, a suture anchor carried by the inserter, a distal tip removably coupled to a distal end of the inserter, and a driver coupled to the inserter, wherein the suture anchor, inserter, distal tip and driver are concentric about a central longitudinal axis of the flexible member securing assembly and the suture is positioned between the suture anchor and distal tip within the slot while extending neither through the suture anchor nor the distal tip, a combination of the slot and the distal tip forming the openable eyelet;
advancing the inserter into a hole in the bone using the driver to position a distal end of the suture anchor relative to an outer surface of the bone, the distal tip, the opening of the slot and a portion of the suture loaded therein being positioned in the hole;
tensioning the suture relative to the slot and the soft tissue;
actuating a lock member associated with the driver to allow movement of the driver relative to the inserter;
advancing the driver relative to the inserter in a first direction to drive the suture anchor about the inserter into the hole and compress the suture between the distal end of the suture anchor and the distal tip and secure the suture anchor and the suture to the bone without forming a knot in the suture; and
moving the driver in a second direction opposite the first direction to remove the inserter from the hole and the distal tip, suture anchor and the suture, the moving step uncoupling the distal tip from the inserter, opening the openable eyelet, and causing the suture to move through the opening of the slot of the openable eyelet as the inserter is removed from the hole.

16. The method of claim 15, further comprising piercing the outer surface of the bone with the distal tip while the inserter is coupled to the suture, the suture anchor and the driver; and
wherein advancing the inserter into the hole in the bone using the driver to position the distal end of the suture anchor relative to the outer surface of the bone includes advancing the inserter relative to the outer surface of the bone using the driver to form the hole in the bone and position the distal end of the suture anchor outside of the hole and adjacent to the outer surface of the bone while the removably coupled distal tip is within the hole.

17. The method of claim 16, wherein advancing the driver to secure the suture anchor and the suture to the bone without forming a knot in the suture includes compressing the suture between an outer surface of the suture anchor and a wall of the hole in the bone.

18. The method of claim 17, wherein actuating the lock member associated with the driver to allow movement of the driver relative to the inserter includes disengaging the lock member from engagement with the inserter at a first position; and
wherein advancing the driver relative to the inserter in the first direction to drive the suture anchor about the inserter into the hole includes the lock member automatically engaging the inserter at a second position spaced apart from the first position and corresponding to a predetermined insertion depth of the suture anchor into the bone.

19. The method of claim 18, wherein moving the driver in a second opposite direction to remove the inserter from the hole, the suture anchor and the suture includes moving the driver in the second opposite direction after the lock member automatically engages the inserter at the second position.

20. The method of claim 18, wherein disengaging the lock member includes moving a depressible member to disengage the lock member from engagement with the inserter at the first position, where the inserter extends through the depressible member.

21. The method of claim 15, wherein advancing the driver relative to the inserter in a first direction to drive the suture anchor about the inserter includes positioning the suture between first and second projections extending from a proximal end of the distal tip.

22. The method of claim 21, wherein the first and second projections are spaced apart and orientated relative to the slot such that the suture can be moved by the suture anchor relative to the slot and into a space between the first and second projections such that the suture can be positioned between the first and second projections by the suture anchor while the distal tip is removably coupled to the inserter.

23. A flexible member securing assembly for use in securing a flexible member relative to bone, the assembly comprising:
   a flexible member;
   an inserter having a body extending along a longitudinal axis from a proximal end to a distal end;
   a driver assembly including a handle and a drive member coupled to the handle, the proximal end of the inserter positioned in an internal bore of the drive member and the handle;
   a lock arrangement associated with the driver assembly and configured to selectively lock the inserter to the driver assembly in one of a plurality of positions, the inserter extending through a portion of the lock arrangement;
   an anchor slidably carried on the inserter, wherein the inserter, driver assembly and anchor are concentric about the longitudinal axis;
   a slot formed in the inserter proximate the distal end, the slot being configured to receive the flexible member and selectively retain the flexible member therein; and
   a distal tip removably coupled to the distal end of the inserter such that the flexible member is coupled to the inserter between the distal tip and the anchor while extending neither through the distal tip nor the anchor, wherein a combination of the slot and the distal tip form an openable eyelet configured to retain the flexible member, and wherein, when the distal tip is removed from the distal end of the inserter, the slot defines an opening proximate the distal end of the inserter that is sized to allow the flexible member to pass through the opening;
   wherein the distal tip is adapted to form a pilot hole in the bone via a force applied to the driver assembly and the driver assembly is adapted to insert the anchor into the pilot hole about the inserter and into substantial engagement with the distal tip to secure the anchor and flexible member to the bone without forming a knot in the suture.

24. The assembly of claim 23, wherein the lock arrangement is associated with the handle and includes a lock member selectively engagable with the inserter in a first position of the plurality of positions in which the driver assembly is fixed to the inserter, the driver assembly rotatably and axially movable relative to the inserter upon releasing the lock member from engagement at the first position.

25. The assembly of claim 24, wherein the driver assembly is configured to be advanced relative to the inserter and is adapted to insert the anchor into the bone to a predetermined depth at which the lock member automatically engages the inserter at a second position of the plurality of positions axially spaced apart from the first position to fix the driver assembly to the inserter.

26. The assembly of claim 23, wherein the distal tip includes a pointed distal end and a proximal end having first and second projections extending axially therefrom, the first and second projections configured to align with the slot when the distal tip is coupled to the inserter.

27. The assembly of claim 26, wherein the distal tip is adapted to receive a portion of the flexible member between the first and second projections.

* * * * *